(12) United States Patent
Levitan (10) Patent No.: US 8,887,717 B2
(45) Date of Patent: Nov. 18, 2014

(54) INTRODUCER FOR SURGICAL AIRWAY CATHETERS

(75) Inventor: Richard M. Levitan, Radnor, PA (US)

(73) Assignee: Airway Cam Technologies, Inc., Wayne, PA (US)

( * ) Notice: Subject to any disclaimer, the term of this patent is extended or adjusted under 35 U.S.C. 154(b) by 242 days.

(21) Appl. No.: 13/484,933

(22) Filed: May 31, 2012

(65) Prior Publication Data

US 2012/0298102 A1 Nov. 29, 2012

Related U.S. Application Data

(63) Continuation-in-part of application No. 13/501,602, filed as application No. PCT/US2010/052798 on Oct. 15, 2010.

(60) Provisional application No. 61/251,776, filed on Oct. 15, 2009.

(51) Int. Cl.
*A61M 16/00* (2006.01)
*A62B 9/06* (2006.01)
*A61M 16/04* (2006.01)
*A61B 17/3209* (2006.01)
*A61B 17/3211* (2006.01)

(52) U.S. Cl.
CPC ........ *A61M 16/0472* (2013.01); *A61B 17/3209* (2013.01); *A61B 2017/32113* (2013.01)
USPC ............. 128/200.26; 128/207.14; 128/207.29

(58) Field of Classification Search
CPC ..................... A61M 16/0465; A61M 16/0472; A61M 25/06; A61M 2025/0656; A61M 25/0687; A61M 29/00
USPC ............. 128/200.26, 207.14, 207.15, 207.29; 606/167, 185, 191, 198; 604/506, 508, 604/510, 164.01, 164.03, 164.1, 164.11, 604/170.02, 264
See application file for complete search history.

(56) References Cited

U.S. PATENT DOCUMENTS 2,865,374 A * 12/1958 Brown et al. ............ 128/207.29
2,991,787 A    7/1961 Shelden et al.

(Continued)

OTHER PUBLICATIONS

European Office Action; Mailed Mar. 8, 2013 for corresponding EP Application No. EP 10 771 284.6.

(Continued)

*Primary Examiner* — Kristen Matter
(74) *Attorney, Agent, or Firm* — Mendelsohn, Drucker & Dunleavy, P.C.; Steve Mendelsohn (57) ABSTRACT

An introducer for a surgical airway catheter has a proximal handle; a curved, rod-shaped main section; an opening-enlarging region; and a rod-shaped distal tip, sized to receive the catheter tube. After making an initial opening in a patient's trachea, the operator inserts the distal tip into the initial opening up to the cutting region. The operator uses the opening-enlarging region to sufficiently widen the opening by moving the introducer from side to side or simply by inserting the introducer into the opening to enable the widened opening to receive the tube and cuff of the catheter. The operator rotates the introducer and catheter into the trachea through the widened opening and then removes the introducer leaving the catheter in place. The introducer and catheter can be pre-configured in a surgical kit having a retractable scalpel configurable onto the introducer's handle and used to excise the initial tracheal opening.

34 Claims, 5 Drawing Sheets

(56) References Cited

U.S. PATENT DOCUMENTS

| | | | | |
|---|---|---|---|---|
| 3,334,631 A | * | 8/1967 | Stebleton | 128/200.26 |
| 3,556,103 A | * | 1/1971 | Calhoun et al. | 128/207.29 |
| 3,957,055 A | * | 5/1976 | Linder et al. | 128/200.26 |
| 3,968,800 A | * | 7/1976 | Vilasi | 606/198 |
| 4,246,897 A | | 1/1981 | Muto | |
| 5,186,168 A | | 2/1993 | Spofford et al. | |
| 5,217,005 A | | 6/1993 | Weinstein | |
| 5,279,285 A | | 1/1994 | Griggs | |
| 5,429,127 A | * | 7/1995 | Kolobow | 128/207.14 |
| 5,507,279 A | * | 4/1996 | Fortune et al. | 128/200.26 |
| 5,546,936 A | * | 8/1996 | Virag et al. | 128/207.14 |
| 5,546,937 A | * | 8/1996 | Stuart et al. | 128/207.15 |
| 5,928,198 A | * | 7/1999 | Lester | 604/164.04 |
| RE36,611 E | | 3/2000 | French | |
| 6,481,436 B1 | * | 11/2002 | Neame | 128/200.26 |
| 6,637,435 B2 | | 10/2003 | Ciaglia et al. | |
| 2005/0279363 A1 | | 12/2005 | Cruz | |
| 2006/0124134 A1 | * | 6/2006 | Wood | 128/207.29 |
| 2008/0017195 A1 | * | 1/2008 | Yoshida | 128/200.26 |
| 2008/0257359 A1 | * | 10/2008 | Rumsey | 128/207.29 |
| 2009/0050146 A1 | * | 2/2009 | Smith | 128/200.26 |
| 2010/0012130 A1 | | 1/2010 | Guerra | |
| 2010/0108060 A1 | * | 5/2010 | Pecherer et al. | 128/200.26 |

OTHER PUBLICATIONS

Paladino, L., et al., "Development of a Rapid, Safe, Fiber-Optic Guided, Single-Incision Cricothyrotomy Using a Large Ovine Model: A Pilot Study", Resuscitation, Elsevier, IE, vol. 80, No. 9, Sep. 1, 2009, pp. 1066-1069, XP026460486.

International Search Report; Mailed Jan. 18, 2011 for corresponding PCT Application No. PCT/US2010/052798.

* cited by examiner

INTRODUCER FOR SURGICAL AIRWAY CATHETERS

CROSS-REFERENCE TO RELATED APPLICATIONS

This application is a continuation-in-part of U.S. patent application Ser. No. 13/501,602, filed on Apr. 12, 2012, which claims the benefit of the filing date of PCT application no. PCT/US10/52798, filed on Oct. 15, 2010, which claims the benefit of the filing date of U.S. provisional application No. 61/251,776, filed on Oct. 15, 2009, the teachings of both of which are incorporated herein by reference in their entirety.

BACKGROUND

1. Field of the Invention

The present invention relates to medical devices and techniques for using medical devices and, more specifically but not exclusively, to an introducer for surgical airway catheters.

2. Description of the Related Art

This section introduces aspects that may help facilitate a better understanding of the invention. Accordingly, the statements of this section are to be read in this light and are not to be understood as admissions about what is prior art or what is not prior art.

Emergency cricothyrotomy or tracheotomy can be performed using a traditional open technique (scalpel and tracheal hook), trochar-type devices, or with a wire-guided percutaneous approach using dilators (a.k.a. Seldinger technique). The preferred emergency surgical airway insertion site is the cricothyroid membrane because it is a relatively large space, it is devoid of large blood vessels, and it is generally accessible regardless of body habitus.

Open techniques involve a skin incision, stabilization of the trachea with either a tracheal hook or other instrument, and subsequent placement of a tracheal tube or surgical airway tube (tracheostomy tube or other short airway catheter) directly into the opening. These techniques are intimidating to providers without formal surgical training. Open techniques require fine motor control under situations of marked duress for operators and extreme time constraints for patients. Examples of these situations include hostile battlefield and tactical situations, in addition to traumatic presentations to emergency departments. Risks include vascular injury of laterally adjacent structures, perforation of the posterior trachea, creation of false subcutaneous passages, and fractures of the thyroid or cricoid cartilages due to the tracheal hook. Open surgical techniques are also technically challenging due to variations in the thickness of anterior neck tissues and bleeding that obscures landmarks. If control of the trachea by the tracheal hook is lost during the procedure, the opening may retract and be difficult to re-identify.

Trochar-type devices use sharp pointed blunt or hollow points to enter the skin and puncture the trachea, after which an airway tube is inserted (either over or through the sharp trochar). Upon insertion, the direction of force is in an anterior to posterior direction. This can cause compression of the trachea (decreasing the anterior posterior dimension) due to sudden and forceful entry into the trachea. The sharp point of such a device may then puncture the thin wall of the posterior trachea. This can result in procedural failure, false passage, mediastinal injury, subcutaneous emphysema, and tension pneumothorax. If the insertion point is off midline, then the great vessels of the neck (carotid artery and jugular vein) may be disrupted resulting in major bleeding. In many clinical situations that require surgical airway access, there is injury to the neck that may distort landmarks and proper identification of midline may be difficult.

Wire-guided percutaneous devices are less intimidating to providers since a needle is used to place a wire into the trachea and no direct skin or tracheal incision is required. A skin or tissue plug in the needle may make identification of the trachea with a needle difficult or impossible. It is also possible to create a false passage with the wire. After the wire is placed, a dilator is used to serve as a stent for a cuffed short airway tube. To pass the dilator, the skin incision must be enlarged. Passage of the dilator and tube involves a relative sharp turn into the trachea. Expanding the skin incision requires cutting down on the wire using fine motor control of the scalpel while holding the wire in place. An inadequate skin incision, or an inappropriate insertion angle of the dilator and tube, may make passage into the trachea mechanically difficult. It can be difficult to control both dilator and tube during forceful insertion over the wire. The percutaneous method requires an average of 100 seconds before the patient can be ventilated. Since there is great reluctance for operators to initiate surgical airways, an additional 100-second delay to ventilation may result in hypoxic injury or death.

SUMMARY

A published article by Paladino, DuCanto, and Manoach describes use of a rigid optical stylet for stabilizing the trachea after neck incision, followed by direct visualization of the trachea through the fiberoptic instrument. See "Development of a rapid, safe, fiber-optic guided, single-incision cricothyrotomy using a large ovine model: a pilot study," Paladino L., DuCanto J., and Manoach S., Resuscitation, 2009 September; 80 (9):1066-9 (Epub 2009 Jul. 15). After the opening is expanded with another scalpel incision, the authors passed a pre-loaded, snug-fitting short airway tube over the stylet into the trachea.

Problems in the prior art are addressed in accordance with the principles of the present invention by providing technique for inserting a surgical airway catheter using an introducer that is simpler than the device described by Paladino et al. and without the need for fiberoptic guidance.

In one embodiment, the present invention is an introducer for inserting a surgical airway catheter into an opening in a patient's trachea. The introducer comprises (i) a handle at a proximal end of the introducer, (ii) a rod-shaped main section connected to the handle, (iii) a cutting region connected to the main section, and (iv) a rod-shaped distal tip connected to the cutting region. The cutting region enables an operator of the introducer to widen an initial opening in the trachea by moving the introducer from side to side after inserting the distal tip inserted into the opening in the trachea and with the cutting region positioned at the opening.

In another embodiment, the present invention is a sealed surgical kit for inserting a surgical airway catheter into an opening in a patient's trachea. The surgical kit comprises the catheter and an introducer as described above.

In yet another embodiment, the present invention is a method for inserting a surgical airway catheter into an opening in a patient's trachea. The method comprises (a) excising an initial opening in the trachea. (b) inserting a distal tip of an introducer into the initial opening with the catheter pre-configured on the introducer, (c) widening the opening using a cutting region of the introducer, and (d) rotating the introducer and catheter into the trachea through the widened opening and then removing the introducer.

BRIEF DESCRIPTION OF THE DRAWINGS

Other aspects, features, and advantages of the present invention will become more fully apparent from the following

DETAILED DESCRIPTION

Figure 1A:
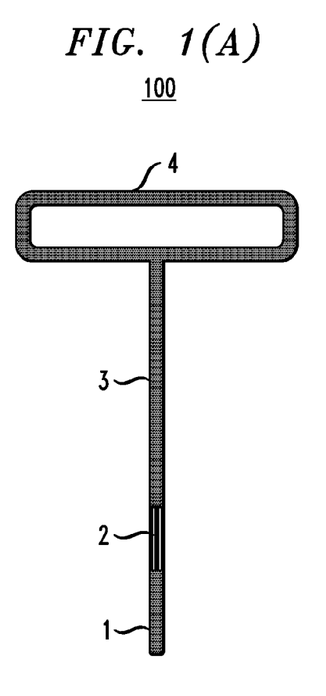
FIGS. 1(A) and 1(B) show front and perspective views, respectively, of an introducer according to one embodiment of the present invention.
Figure 1B:
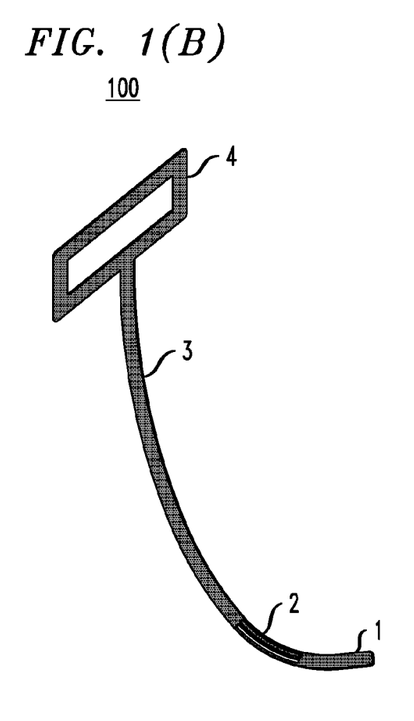

FIGS. 1(A) and 1(B) show front and perspective views, respectively, of an introducer 100 according to one embodiment of the present invention. As shown, introducer 100 has handle 4, main section 3, cutting region 2, and distal tip 1. Introducer 100 can be made from a rod of suitable material, such as metal (e.g., steel or aluminum) or plastic.

Figure 2:
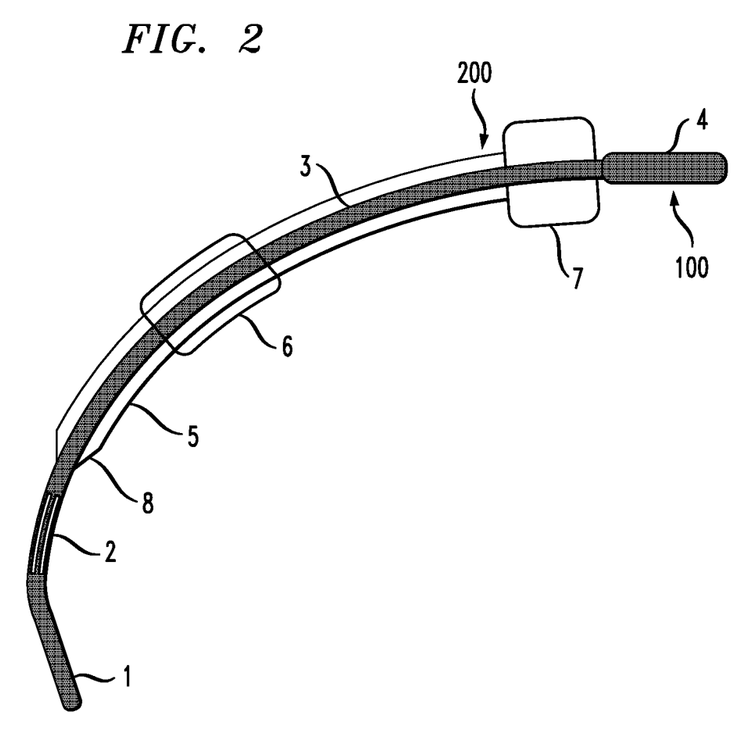
FIG. 2 shows a cross-sectional side view of the introducer of FIG. 1 inserted into a surgical airway catheter.

FIG. 2 shows a cross-sectional side view of introducer 100 of FIG. 1 inserted into a surgical airway catheter 200. As shown, catheter 200 has a flexible tube 5 with a standard 15-mm connector 7 at one end that, after withdrawal of the introducer) can be connected to a manual resuscitator (a.k.a. a bag valve mask or an Ambu bag) or a ventilatory circuit. The catheter has a taper 8 at the other end and an intermediate cuff 6 for sealing the trachea upon inflation of the cuff. The outer dimensions of the thin, round, rod-shaped main section 3, cutting region 2, and thin, round, rod-shaped distal tip 1 of introducer 100 closely approximate the inner dimensions of flexible tube 5 of catheter 200.

Figure 3A:
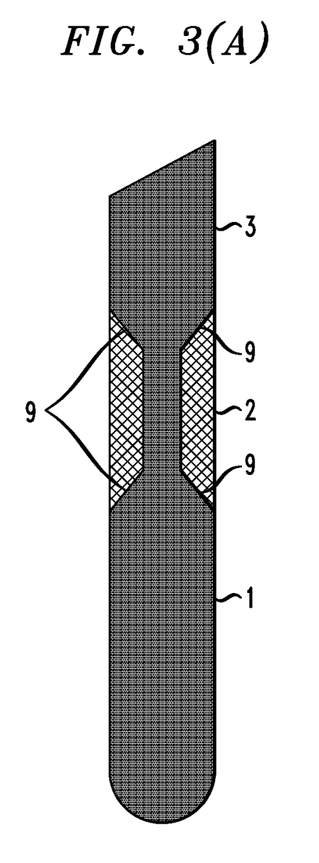
FIGS. 3(A)-(E) show different views of the distal tip, the cutting region, and/or a portion of the main section of the introducer of FIG. 1.
Figure 3B:
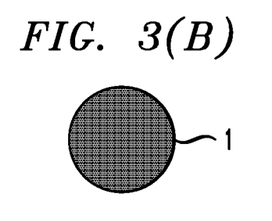
Figure 3C:
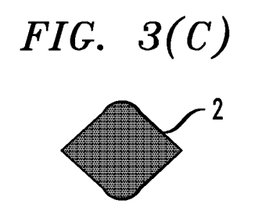
Figure 3D:
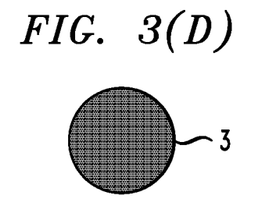
Figure 3E:
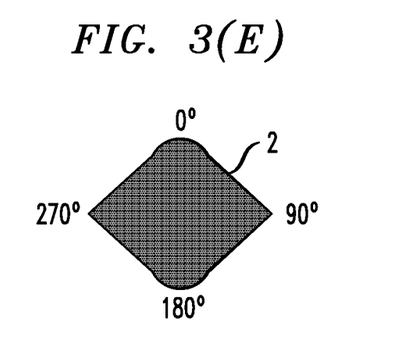

FIG. 3(A) shows an enlarged front view of distal tip 1, cutting region 2, and a portion of main section 3 of introducer 100 of FIG. 1. FIGS. 3(B), 3(C), and 3(D) show lateral cross-sectional views of distal tip 1, cutting region 2, and main section 3, respectively. FIG. 3(E) shows an enlarged version of the lateral cross-sectional view of cutting region 2 of FIG. 3(C).

Figure 4A:
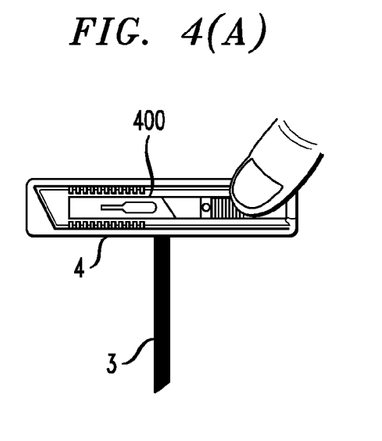
FIGS. 4(A)-(B) show front views of a portion of the introducer of FIG. 1 according to a particular implementation in which the handle of the introducer has an integrated, retractable scalpel.
Figure 4B:
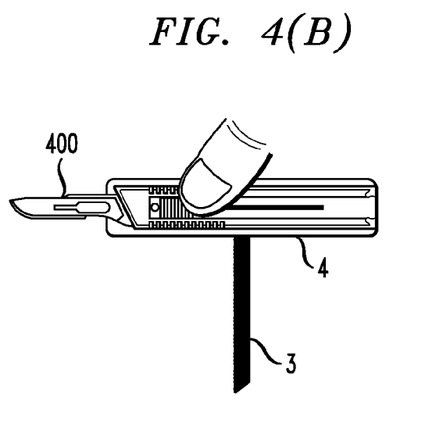

FIGS. 4(A) and 4(B) show front views of a portion of introducer 100 of FIG. 1 according to a particular implementation in which handle 4 has an integrated, retractable scalpel 400. In particular, FIG. 4(A) shows scalpel 400 with its blade in a retracted position, while FIG. 4(B) shows scalpel 400 with its blade in an extended position, as controlled by the thumb of an operator of introducer 100.

Catheter 200 is flexible enough to easily insert into an incision in the neck and trachea. Introducer 100 should be of sufficient diameter so there is no gap between the outer surface of main section 3 of the introducer and the inner surface of tube 5 of the catheter, but not too tight as to inhibit easy sliding of the catheter off of the introducer. A good fit between the introducer and the catheter is also helpful for inserting the introducer and the catheter as a unit into an incision in the neck and into an opening in the trachea.

Introducer 100 has an overall curved shape facilitating both storage and easy passage of a short surgical airway catheter, such as catheter 200. The proximal end of introducer 100 has a T-shape that forms handle 4. Main section 3 of introducer 100 has a gentle curve of sufficient length to match an appropriately sized surgical airway. Main section 3 may be made more or less flexible based on the rod material selected to form introducer 100. In general, main section 3 should have an appropriate balance of flexibility and stiffness to enable efficient insertion of the introducer and catheter into a patient's trachea. As shown in FIG. 2, connector 7 at the proximal end of catheter 200 stops against the T-shaped handle 4. At the distal end of catheter 200, taper 8 provides a tapered fit against main section 3 of introducer 100. As shown in FIGS. 1(B) and 2, distal tip 1 of introducer 100 has (i) an upward bend towards handle 4 of between about 20 degrees and about 40 degrees relative to main section 3 and (ii) a smooth rounded tip.

Cutting region 2, located between distal tip 1 and main section 3 of introducer 100, is a short section of rod that has a diamond-shaped cross-sectional appearance, as shown in FIGS. 3(C) and 3(E). The diamond-shaped cutting region 2 has four edges corresponding to 0 degrees, 90 degrees, 180 degrees, and 270 degrees, as represented in FIG. 3(E). When inserted into a patient, the 0-degree edge is anterior, the 180-degree edge is posterior, and the 90- and 270-degree edges correspond to the patient's left and right sides. The distance between the 0-degree and 180-degree edges approximates the diameter of the rod used to form distal tip 1 and main section 3. The distance between the edges at 90 degrees and 270 degrees does not exceed that rod diameter. The 0- and 180-degree edges (i.e., the anterior and posterior edges) have smooth surfaces. In contrast, the lateral edges (i.e., at 90 degrees and 270 degrees) of the diamond-shaped cutting region 2 are sharp enough to expand a horizontal (e.g., from patient right to patient left) incision made in the trachea, but not so sharp as to easily cut the operator's skin if accidentally touched. Note that, as shown in FIG. 3(A), the sharp lateral edges are tapered (9) at both sides and both ends to meet the rounded rods above and below. Coupled with the rounded 0- and 180-degree edges (which match the rod's diameter), the taper 8 at the distal end of catheter 200 will not catch as it slides over the diamond-shaped cutting region 2 of introducer 100, either upon loading the catheter or advancing it off of the introducer. The edges at 90 degrees and 270 degrees are also not sharp enough to cut into the airway catheter. In alternative embodiments, one or both of the dimensions of the diamond-shaped cutting region 2 may be smaller than the rod diameter.

For certain implementations, cutting region 2 may be made entirely of the same rod material as the other elements of introducer 100. For those implementations, the rod material must be pressed or molded into the shape shown in FIG. 3 to provide both the sharp lateral edges and the smooth anterior and posterior edges. For other implementations, cutting region 2 may be a composite of different materials. For example, the smooth edges may be formed of the same (e.g., plastic) material used for the other elements of the introducer, while the sharp edges may be metal blades mounted in that plastic material.

Handle 4 of the introducer has dimensions sufficient to allow an easy grip. In the embodiment of introducer 100, the handle is symmetric in shape in both its long axis (i.e., perpendicular to the longitudinal axis of the introducer's main section 3 and its short axis (i.e., parallel to the longitudinal axis of main section 3). The handle is of sufficient length such that the housing of a retractable scalpel, such as retractable scalpel 400 of FIG. 4, could be snapped or secured onto the top of the handle, with the scalpel blade pointing in either direction allowing single-finger control, as represented in FIG. 4. In the configuration shown in FIG. 4, the operator's right thumb is extending the scalpel blade toward the left. An alternative configuration could have the scalpel oriented on the handle to allow a left-handed operator the ability to extend the scalpel blade in the other direction.

In the intended use of introducer 100, the operator's non-dominant hand is used to identify laryngeal landmarks and stabilize the trachea and thyroid cartilage. The operator can be either at the patient's side or at the head of the bed above the supine patient. A retractable scalpel, such as retractable scalpel 400 of FIG. 4, is secured longitudinally in the handle (as shown in FIG. 4) and oriented to match the intended right- or left-hand use of the operator. Introducer 100 is held by handle 4 in the operator's dominant hand with the tips of the thumb and first two or three fingers of that dominant hand surrounding main section 3. The thumb can be moved out or in on top of the scalpel to either extend or retract the blade.

After the scalpel blade is exposed by the operator's dominant thumb (as in FIG. 4(B)), a small, initial, horizontal (e.g., from patient left to patient right for a right-handed operator) incision is made into the trachea of a size to permit insertion of the distal tip 1 of the introducer. The scalpel blade is then retracted into a safe position by the operator's thumb (as in FIG. 4(A)). The rounded distal tip 1 of the introducer is inserted into the small opening in the trachea. The rigidity of the overall introducer and the rounded curvature allow the distal tip to be curved into the trachea. Upon insertion, the only portions of the introducer that can touch the posterior trachea (e.g., distal tip 1, the 180-degree edge of cutting region 2, and main section 3) are smooth and rounded to prevent puncture of the posterior trachea. The anterior (0-degree) edge of the diamond-shaped cutting region 2 is also smooth and rounded to prevent damage to the anterior cricoid ring.

Handle 4 is used to lift up and control the trachea in a manner that gives the operator tactile confirmation of proper entry into the trachea, e.g., when partially retracting the introducer from the opening. If the distal tip of the introducer is under the skin, but not in the trachea, then the neck skin will tent and feel different from when the trachea is being properly controlled. By tilting the distal tip of the introducer anteriorly within the trachea, and also up and down inside the trachea, the operator feels the rounded distal tip riding over the anterior tracheal rings. With tactile feedback from both tracheal control and the tip interaction with the rings, the tracheal location of the device is assured.

The next step involves a quick side-to-side (i.e., between patient left and patient right) movement of the introducer contacting the sharpened lateral (i.e., 90- and 270-degree) edges of the diamond-shaped cutting region 2 with the lateral margins of the initial opening into the trachea. By this side-to-side movement, the opening into the trachea is expanded without the need for a scalpel or Trousseau dilator. Since the outer diameters of the catheter's tube 5 and cuff 6 are larger than the diameter of the distal tip 1 of the introducer, enlarging the opening will enable passage of the catheter's tube and cuff into the trachea. With the distal tip 1 in the trachea, and the opening expanded as described, the operator's other hand is used to push the pre-loaded short airway tube 5 along with cuff 6 off the introducer and fully into the trachea (up to connector 7). After insertion of airway catheter 200, introducer 100 is rotated backward out of the trachea, and the airway catheter is secured. Alternatively, it is possible to fully advance the introducer and the catheter as a unit into the trachea up to connector 7, and then withdraw the introducer leaving the catheter in place.

Figure 5:
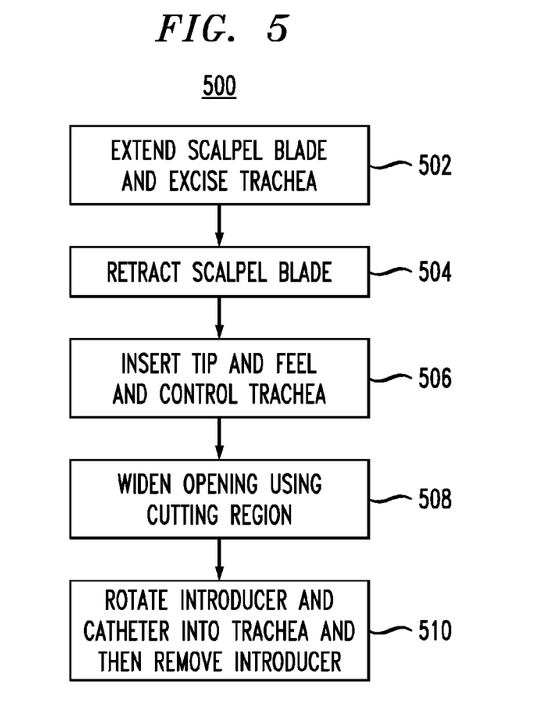
FIG. 5 shows a flow diagram of a method for using the introducer of FIG. 1.

FIG. 5 shows a flow diagram of a method 500 for using introducer 100 of FIG. 1 already configured with catheter 200 and retractable scalpel 400. At step 502, the operator extends the scalpel blade and excises the trachea. At step 504, the operator retracts the scalpel blade. At step 506, the operator inserts distal tip 1 and uses the introducer to feel and control the trachea. At step 508, the operator widens the initial opening using the diamond-shaped edges of cutting region 2. At step 510, the operator rotates the introducer and the airway catheter into the trachea through the widened opening and removes the introducer leaving the catheter in place.

The dimensions of introducer 100 can be designed to fit, e.g., larger surgical airway catheters for adult patients or smaller surgical airway catheters for pediatric patients. Introducer 100 can also be used to replace tracheotomy tubes that have fallen out.

Embodiments of the present invention, such as introducer 100, can provide one or more of the following advantages:

1) Only three separate items are needed (i.e., introducer 100, catheter 200, and retractable scalpel 400). Since the tube can be pre-loaded on the introducer, there would be only two pieces of equipment when initially opening a sealed surgical kit for the introducer (i.e., the scalpel and the combined tube and introducer). Moreover, since most people are right-handed, the scalpel can also come pre-assembled into the introducer's handle in the configuration suitable for a right-handed operator. In any case, with a retractable scalpel either attached to or built into the handle, the three components become one piece of equipment to hold. This compares to a standard surgical kit that involves at least three loose items, e.g., a tracheal hook, a scalpel, an airway tube, and possibly other retractors. Percutaneous wire-guided devices have many more items, e.g., a needle, a syringe, a wire, a scalpel, an airway tube, and a dilator. Introducer 100 can be packed in a hermetically sealed surgical kit with a scalpel and airway catheter, where the kit can be compressed without any significant risk to proper function. There is nothing to break with the pre-loaded airway tube on the introducer. There are also no exposed sharp points that can puncture other items in a medical kit or an operator if the device is stored in a leg pocket or waist belt bag. This is in contradistinction to tracheal hooks, needles, trochar systems, etc.

2) The trachea is incised initially without significant force, lessening the risk of injury to the posterior wall. Only a small, initial incision is need in the anterior trachea to introduce the small round tip of the introducer. The introducer is then used to lift and control the trachea, so that, when the catheter tube is advanced down, the tube is not being directed at the posterior wall upon insertion.

3) Apart from the initial cut into the trachea, there is no need for repeat use of the scalpel. With some methods, a scalpel is used for initial skin incision and also to enlarge the tracheal opening after something has been placed into the opening. With the percutaneous technique, the scalpel is used initially to nick the skin and again to widen the opening adjacent to the wire. The sharpened lateral edges of the introducer's cutting region 2 provide widening of the initial opening without having to pick up the scalpel again. This is much faster and eliminates the need for fine hand control. It also eliminates the problem of losing or contaminating the scalpel after putting it down. Compared to any other means of surgical airway access, there is a marked reduction in the number of fine motor steps involved in the present invention.

4) The introducer and method involve no articulating parts and no springs. As noted, a retractable scalpel could be incorporated into the handle and easily controlled by thumb extension or flexion. Disposable surgical scalpels with retractable blades or guards are in common use.

5) There is a reduced risk of passing a tube into a false passage. If the tip of the introducer is not in the trachea, then the trachea will not be palpably controlled with side-to-side movements, and the rings will not be felt with up and down tip movements against the anterior rings. If the tip is in the subcutaneous skin, then the tip will tent up against the skin. This has a much different feel from when the tip is in the trachea.

6) The introducer can be constructed from steel or fashioned from a hardened plastic. It can be simply and inexpensively produced.

7) The operator's non-dominant hand never has to leave the landmarks of the thyroid and neck. The dominant hand never has to let go of the introducer (pre-configured with an integrated scalpel and overlying airway catheter). This permits an operator to perform the procedure without needing an assistant to pass instruments. There are reduced risks of losing a piece of equipment and of provider injury resulting from multiple operators with hands in the surgical field. The net effects of the design and integration of components are decreased time until intubation is achieved and improved safety for both operator and patient. From an instructional perspective, the method is much simpler to teach and ergonomically easier to learn than any other method of inserting a surgical airway.

In certain embodiments, the introducer is made from a solid rod. In other embodiments, the introducer is made from a hollow rod that is open both at the handle and at the distal tip. Note that the opening at the distal tip can be either at the end of the distal tip or along the side of the distal tip. If made from a hollow rod, when the introducer is inserted into the trachea of a breathing patient, air may pass through the hollow rod from the opening at the distal tip to the opening at the handle. Such air flow may produce an audible sound that would provide additional confirmation to the operator that the introducer was successfully inserted into the trachea. In addition, the rod opening at the handle may be specifically shaped to function as a whistle or a whistle may be attached to that handle opening to enhance the audible sound produced.

Figure 6A:
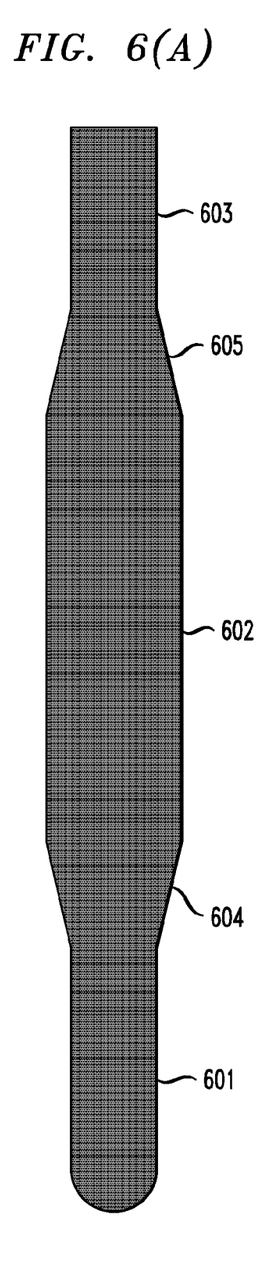
FIGS. 6(A)-(G) show different views of the distal tip, the opening-enlarging region, and a portion of the main section of alternative introducers according to different embodiments of the present invention.
Figure 6B:
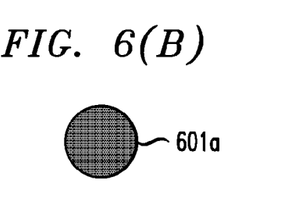
Figure 6C:
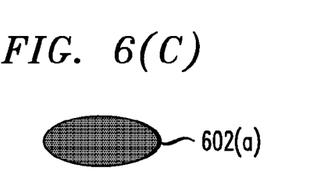
Figure 6D:
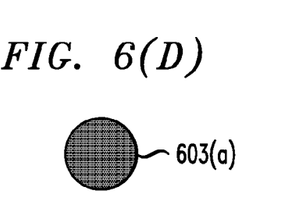
Figure 6E:
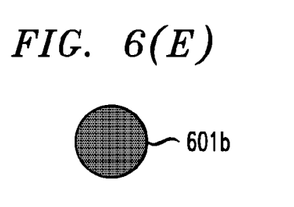
Figure 6F:
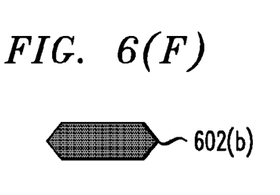
Figure 6G:
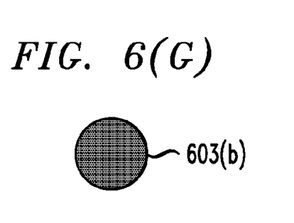

FIG. 6(A) shows an enlarged front view of distal tip 601, opening-enlarging region 602, and a portion of main section 603 of alternative introducers according to different embodiments of the present invention. FIGS. 6(B), 6(C), and 6(D) show lateral cross-sectional views of distal tip 601(a), opening-enlarging region 602(a), and main section 603(a), respectively, of a first alternative introducer, while FIGS. 6(E), 6(F), and 6(G) show lateral cross-sectional views of distal tip 601 (b), opening-enlarging region 602(b), and main section 603 (b), respectively, of a second alternative introducer. As shown in FIG. 6(C), opening-enlarging region 602(a) of the first alternative introducer has a rounded, elliptical shape, while opening-enlarging region 602(b) of the second alternative introducer has an elongated, hexagonal shape with opposing cutting edges along its widest dimension, as shown in FIG. 6(F).

As shown in FIGS. 3(A) and 3(E), the widest dimension of cutting region 3 of introducer 100 (i.e., from 90° to 270° in FIG. 3(E)) is no bigger than the diameters of distal tip 1 and main section 3. As shown in FIGS. 6(A)-(G), however, the widest dimension of opening-enlarging region 602 in the two alternative introducers is greater than the diameters of distal tip 601 and main section 603.

As described previously, when properly positioned and moved side to side, cutting region 3 of introducer 100 functions as an opening-enlarging region that enlarges the initial opening into the trachea. Opening-enlarging regions 602(a) and 602(b) of the two alternative introducers can perform the same function of enlarging the initial opening without having to (i) pause or slow the longitudinal insertion motion of the introducer and/or (ii) move the introducer from side to side within the initial opening. Rather, when the initial opening is smaller than the widest dimension of the opening-enlarging region 602, the initial opening will be enlarged merely by inserting the opening-enlarging region into the initial opening.

As indicated in FIG. 6(A), an introducer according to FIG. 6 has (i) a first transition region 604 between distal tip 601 and region 602 and (ii) a second transition region 605 between region 602 and main section 603. Note that most of the enlarging of the initial opening caused by the insertion of an introducer of FIG. 6 occurs as transition region 604 is inserted into the opening. As such, in yet another embodiment, only transition region 604 has a hexagonal cross section with opposing cutting edges, where every other region has either a circular or elliptical cross section. Such an embodiment may be able to effectively enlarge the opening simply by inserting the introducer longitudinally into the opening, without significant risk of any cutting edges damaging the catheter as the introducer is withdrawn from the opening leaving the catheter in place within the opening.

Furthermore, although FIG. 6 represents embodiments in which the diameter of the main section 603 is smaller than the width of opening-enlarging region 602, in alternative embodiments, the diameter of the main section is approximately the same as the width of the opening-enlarging region. In some of these embodiments, the main section has the same (e.g., elliptical) shape as the opening-enlarging region, such that there is no distinct transition between the two regions.

One of the characteristics of an introducer having a region or section with an elliptical (or otherwise elongated) cross section, such as region 602 of FIG. 6, is that the introducer will be mechanically more rigid side to side and will allow more flexion anteriorly and posteriorly. These mechanical properties provide advantages for inserting an introducer into an airway. Another way to achieve this mechanical asymmetry is to implement the region or section using a relatively flexible, outer, cylindrical member with a more-rigid, internal rod having the elliptical (or otherwise elongated) cross section.

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain the nature of this invention may be made by those skilled in the art without departing from the scope of the invention as expressed in the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. An introducer for inserting a surgical airway catheter into a tracheotomy opening in a patient's trachea, the introducer comprising:
   a handle at a proximal end of the introducer;
   a rod-shaped main section connected to the handle;
   an opening-enlarging region connected to the main section; and
   a rod-shaped distal tip connected to the opening-enlarging region, wherein:
      the opening-enlarging region has a non-circular cross-section having (i) a smallest cross-sectional dimension smaller than a cross-sectional diameter of the distal tip and (ii) a largest cross-sectional dimension larger than the cross-sectional diameter of the distal tip; and
      the opening-enlarging region enables an operator of the introducer to widen an initial tracheotomy opening in the trachea by inserting first the distal tip into the initial tracheotomy opening and then the opening-enlarging region, whereby transition from the cross-sectional diameter of the distal tip to the largest cross-sectional dimension of the opening-enlarging region causes the initial tracheotomy opening to widen.

2. The introducer of claim 1, wherein the handle is designed to receive a retractable scalpel that can be used by the operator to excise the initial opening in the trachea, wherein the initial opening is large enough to receive the distal tip of the introducer.

3. The introducer of claim 2, wherein the handle is adapted to receive the retractable scalpel in either a right-handed configuration or an opposing, left-handed configuration wherein the scalpel can be selectively configured such that a blade of the scalpel is extendable in one direction relative to the handle for the right-handed configuration and in the opposite direction for the left-handed configuration.

4. The introducer of claim 1, wherein outer dimensions of the main section, the opening-enlarging region, and the distal tip of the introducer are designed to be inserted into the catheter.

5. The introducer of claim 1, wherein:
   the catheter has a tube and a cuff positioned over the tube; and
   the opening-enlarging region is designed to sufficiently widen the opening for receiving the tube and the cuff of the catheter.

6. The introducer of claim 1, wherein:
   the opening-enlarging region is a cutting region; and
   the cutting region enables the operator of the introducer to widen the initial opening in the trachea by moving the introducer from side to side after inserting the distal tip into the opening in the trachea and with the cutting region positioned at the opening.

7. The introducer of claim 6, wherein the cutting region has (i) two opposing, cutting edges and (ii) two opposing, rounded edges oriented 90 degrees from the cutting edges.

8. The introducer of claim 7, wherein ends of the two cutting edges are beveled at connections to the main section and the distal tip.

9. The introducer of claim 1, wherein the main section of the introducer has a curved shape that enables the distal tip, the opening-enlarging region, and the main section of the introducer to be rotated into the trachea through the opening.

10. The introducer of claim 9, wherein the distal tip is bent towards the handle at an angle between about 20 degrees and about 40 degrees relative to a longitudinal axis of the opening-enlarging region.

11. The introducer of claim 1, wherein the introducer is hollow with openings at the distal tip and handle to enable air to flow through the introducer producing an audible sound.

12. The introducer of claim 1, wherein:
   the opening-enlarging region is a cutting region;
   the handle is designed to receive a retractable scalpel that can be used by the operator to excise the initial opening in the trachea, wherein the initial opening is large enough to receive the distal tip and the cutting region of the introducer;
   the handle is adapted to receive the retractable scalpel in either a right-handed configuration or an opposing, left-handed configuration wherein the scalpel can be selectively configured such that a blade of the scalpel is extendable in one direction relative to the handle for the right-handed configuration and in the opposite direction for the left-handed configuration;
   outer dimensions of the main section, the cutting region, and the distal tip of the introducer are designed to be inserted into the catheter;
   the catheter has a tube and a cuff positioned over the tube;
   the cutting region is designed to sufficiently widen the opening for receiving the tube and the cuff of the catheter;
   the cutting region has (i) two opposing, cutting edges and (ii) two opposing, rounded edges oriented 90 degrees from the cutting edges;
   ends of the two cutting edges are beveled at connections to the main section and the distal tip; and
   the main section of the introducer has a curved shape that enables the distal tip, the cutting region, and the main section of the introducer to be rotated into the trachea through the opening.

13. The introducer of claim 1, wherein the opening-enlarging region comprises an oval cross-section.

14. The introducer of claim 1, wherein the opening-enlarging region comprises two opposing cutting edges.

15. The introducer of claim 1, wherein a transition region between the distal tip and the opening-enlarging region comprises two opposing cutting edges.

16. The introducer of claim 1, wherein:
   the handle is designed to receive a retractable scalpel that can be used by the operator to excise the initial opening in the trachea, wherein the initial opening is large enough to receive the distal tip of the introducer;
   the handle is adapted to receive the retractable scalpel in either a right-handed configuration or an opposing, left-handed configuration wherein the scalpel can be selectively configured such that a blade of the scalpel is extendable in one direction relative to the handle for the right-handed configuration and in the opposite direction for the left-handed configuration;
   outer dimensions of the main section, the opening-enlarging region, and the distal tip of the introducer are designed to be inserted into the catheter;
   the catheter has a tube and a cuff positioned over the tube;
   the opening-enlarging region is designed to sufficiently widen the opening for receiving the tube and the cuff of the catheter; and the main section of the introducer has a curved shape that enables the distal tip, the opening-enlarging region, and the main section of the introducer to be rotated into the trachea through the opening.

17. A sealed surgical kit for inserting a surgical airway catheter into a tracheotomy opening in a patient's trachea, the surgical kit comprising:
the catheter; and
an introducer comprising:
a handle at a proximal end of the introducer;
a rod-shaped main section connected to the handle;
an opening-enlarging region connected to the main section; and
a rod-shaped distal tip connected to the opening-enlarging region, wherein:
the opening-enlarging region has a non-circular cross-section having (i) a smallest cross-sectional dimension smaller than a cross-sectional diameter of the distal tip and (ii) a largest cross-sectional dimension larger than the cross-sectional diameter of the distal tip; and
the opening-enlarging region enables an operator of the introducer to widen an initial tracheotomy opening in the trachea by inserting first the distal tip into the initial tracheotomy opening and then the opening-enlarging region, whereby transition from the cross-sectional diameter of the distal tip to the largest cross-sectional dimension of the opening-enlarging region causes the initial tracheotomy opening to widen.

18. The surgical kit of claim 17, wherein the catheter is pre-configured on the introducer prior to being sealed in the surgical kit.

19. The surgical kit of claim 17, further comprising a retractable scalpel that can be used by the operator to excise the initial opening in the trachea, wherein the initial opening is large enough to receive the distal tip of the introducer.

20. The surgical kit of claim 17, wherein the handle is designed to receive the retractable scalpel.

21. The surgical kit of claim 20, wherein the handle is adapted to receive the retractable scalpel in either a right-handed configuration or an opposing, left-handed configuration wherein the scalpel can be selectively configured such that a blade of the scalpel is extendable in one direction relative to the handle for the right-handed configuration and in the opposite direction for the left-handed configuration.

22. The surgical kit of claim 20, wherein the retractable scalpel is pre-configured in the handle of the introducer prior to being sealed in the surgical kit.

23. The surgical kit of claim 17, wherein outer dimensions of the main section, the opening-enlarging region, and the distal tip of the introducer are designed to be inserted into the catheter.

24. The surgical kit of claim 17, wherein:
the catheter has a tube and a cuff positioned over the tube; and
the opening-enlarging region is designed to sufficiently widen the opening for receiving the tube and the cuff of the catheter.

25. The surgical kit of claim 17, wherein:
the opening-enlarging region is a cutting region; and
the cutting region has (i) two opposing, cutting edges and (ii) two opposing, rounded edges oriented 90 degrees from the cutting edges.

26. The surgical kit of claim 25, wherein ends of the two cutting edges are beveled at connections to the main section and distal tip.

27. The surgical kit of claim 17, wherein the main section of the introducer has a curved shape that enables the distal tip, the opening-enlarging region, and the main section of the introducer to be rotated into the trachea through the opening.

28. The surgical kit of claim 27, wherein the distal tip is bent towards the handle at an angle between about 20 degrees and about 40 degrees relative to a longitudinal axis of the opening-enlarging region.

29. The surgical kit of claim 17, wherein the introducer is hollow with openings at the distal tip and handle to enable air to flow through the introducer producing an audible sound.

30. The surgical kit of claim 17, wherein:
the opening-enlarging region is a cutting region;
the handle is designed to receive a retractable scalpel that can be used by the operator to excise the initial opening in the trachea, wherein the initial opening is large enough to receive the distal tip and the cutting region of the introducer;
the handle is adapted to receive the retractable scalpel in either a right-handed configuration or an opposing, left-handed configuration wherein the scalpel can be selectively configured such that a blade of the scalpel is extendable in one direction relative to the handle for the right-handed configuration and in the opposite direction for the left-handed configuration;
outer dimensions of the main section, the cutting region, and the distal tip of the introducer are designed to be inserted into the catheter;
the catheter has a tube and a cuff positioned over the tube;
the cutting region is designed to sufficiently widen the opening for receiving the tube and the cuff of the catheter;
the cutting region has (i) two opposing, cutting edges and (ii) two opposing, rounded edges oriented 90 degrees from the cutting edges;
ends of the two cutting edges are beveled at connections to the main section and the distal tip; and
the main section of the introducer has a curved shape that enables the distal tip, the cutting region, and the main section of the introducer to be rotated into the trachea through the opening.

31. The surgical kit of claim 17, wherein the opening-enlarging region comprises an oval cross-section.

32. The surgical kit of claim 17, wherein the opening-enlarging region comprises two opposing cutting edges.

33. The surgical kit of claim 17, wherein a transition region between the distal tip and the opening-enlarging region comprises two opposing cutting edges.

34. The surgical kit of claim 17, wherein:
the handle is designed to receive a retractable scalpel that can be used by the operator to excise the initial opening in the trachea, wherein the initial opening is large enough to receive the distal tip of the introducer;
the handle is adapted to receive the retractable scalpel in either a right-handed configuration or an opposing, left-handed configuration wherein the scalpel can be selectively configured such that a blade of the scalpel is extendable in one direction relative to the handle for the right-handed configuration and in the opposite direction for the left-handed configuration;
outer dimensions of the main section, the opening-enlarging region, and the distal tip of the introducer are designed to be inserted into the catheter;
the catheter has a tube and a cuff positioned over the tube;
the opening-enlarging region is designed to sufficiently widen the opening for receiving the tube and the cuff of the catheter; and the main section of the introducer has a curved shape that enables the distal tip, the opening-enlarging region, and the main section of the introducer to be rotated into the trachea through the opening.

* * * * *